United States Patent
Sakamoto et al.

(10) Patent No.: US 10,378,977 B2
(45) Date of Patent: Aug. 13, 2019

(54) STRAIN AMOUNT CALCULATION SYSTEM, STRAIN AMOUNT CALCULATION METHOD, AND STORAGE MEDIUM

(71) Applicant: TOYOTA PRODUCTION ENGINEERING, Munakata, Fukuoka Prefecture (JP)

(72) Inventors: Takuya Sakamoto, Munakata (JP); Yuki Ishida, Fukuoka (JP)

(73) Assignee: TOYOTA PRODUCTION ENGINEERING, Munakata (JP)

(*) Notice: Subject to any disclaimer, the term of this patent is extended or adjusted under 35 U.S.C. 154(b) by 0 days.

(21) Appl. No.: 15/878,840

(22) Filed: Jan. 24, 2018

(65) Prior Publication Data

US 2018/0224341 A1    Aug. 9, 2018

(30) Foreign Application Priority Data

Jan. 24, 2017  (JP) .................. 2017-010466

(51) Int. Cl.
| | | |
|---|---|---|
| G01L 1/00 | (2006.01) | |
| G01L 1/24 | (2006.01) | |
| G06T 11/20 | (2006.01) | |
| G06T 7/00 | (2017.01) | |
| G01N 3/08 | (2006.01) | |
| G01N 19/00 | (2006.01) | |

(Continued)

(52) U.S. Cl.
CPC ............... *G01L 1/24* (2013.01); *G01N 3/08* (2013.01); *G01N 19/00* (2013.01); *G06T 7/97* (2017.01); *G06T 11/20* (2013.01); *G01N 21/70* (2013.01); *G01N 21/8803* (2013.01)

(58) Field of Classification Search
CPC .. G01L 1/24; G06T 7/97; G06T 11/20; G01N 3/08; G01N 19/00; G01N 21/70; G01N 21/8803
USPC ........................................................... 73/800
See application file for complete search history.

(56) References Cited

U.S. PATENT DOCUMENTS 7,307,702 B1 * 12/2007 Mathur ..................... G01L 1/24
356/32
9,085,052 B1    7/2015  Georgeson et al.
(Continued)

FOREIGN PATENT DOCUMENTS

| JP | 2001-215157 A | 8/2001 |
|---|---|---|
| JP | 2003-506698 A | 2/2003 |

(Continued)

OTHER PUBLICATIONS

Ishii et al.; "Evaluation Method of Loading Condition Based on the Time Response of Mechanoluminescence"; National Institute of Advanced Industrial Science and Technology (AIST); vol. 79, No. 806, pp. 432-442; May 18, 2013.

(Continued)

*Primary Examiner* — Max H Noori
(74) *Attorney, Agent, or Firm* — Oliff PLC

(57) ABSTRACT

A strain amount calculation system includes an imaging unit, and a strain amount calculation device that acquires an image taken by the imaging unit, measures luminescent brightness from the acquired image, calculates an amount of strain on the object caused by a load on the object, based on a temporal change in the measured luminescent brightness, and outputs information on the calculated strain amount.

8 Claims, 4 Drawing Sheets

(51) Int. Cl.
 *G01N 21/70* (2006.01)
 *G01N 21/88* (2006.01)

(56) References Cited

U.S. PATENT DOCUMENTS

| | | | |
|---|---|---|---|
| 9,983,072 B2 * | 5/2018 | Kim | ............................ G01L 1/24 |
| 2001/0017059 A1 | 8/2001 | Xu et al. | |
| 2007/0186674 A1 * | 8/2007 | Hyodo | .................... G01N 3/068 |
| | | | 73/826 |
| 2008/0232083 A1 | 9/2008 | Xu | |
| 2015/0103333 A1 * | 4/2015 | Yun | ..................... G01N 21/8803 |
| | | | 356/32 |
| 2015/0267107 A1 * | 9/2015 | Zhu | ............................ G01L 1/24 |
| | | | 356/32 |

FOREIGN PATENT DOCUMENTS

| | | |
|---|---|---|
| JP | 2006-284393 A | 10/2006 |
| JP | 2010-002415 A | 1/2010 |
| JP | 2010-190865 A | 9/2010 |
| JP | 2015-075477 A | 4/2015 |
| WO | 01/011311 A1 | 2/2001 |
| WO | 2005/097946 A1 | 10/2005 |

OTHER PUBLICATIONS

Jun. 19, 2018 Office Action issued in Japanese Patent Application No. 2017-010466.

* cited by examiner

STRAIN AMOUNT CALCULATION SYSTEM, STRAIN AMOUNT CALCULATION METHOD, AND STORAGE MEDIUM

INCORPORATION BY REFERENCE

The disclosure of Japanese Patent Application No. 2017-010466 filed on Jan. 24, 2017 including the specification, drawings and abstract is incorporated herein by reference in its entirety.

BACKGROUND

1. Technical Field

The present invention relates to a strain amount calculation system that calculates an amount of strain on an object, a strain amount calculation method, and a storage medium.

2. Description of Related Art

In recent years, computer-aided engineering (CAE) has been often used in designing various products and parts. CAE-based design processes include inspection on resistance to stress etc.

One possible technique for measuring a stress on an object is to use a stress measurement system that calculates a stress on an object to be measured (e.g., see Japanese Patent Application Publication No. 2006-284393 (JP 2006-284393 A)). The stress measurement system described in JP 2006-284393 A detects the luminescent intensity of a mechanoluminescent substance attached to an object to be measured, calculates a three-dimensional shape of the object by taking images thereof with a plurality of imaging devices, and corrects the luminescent intensity based on the three-dimensional shape.

SUMMARY

In some cases, calculation results of CAE are verified through a comparison between a stress calculated by CAE and a stress put on an actual product or part. However, a stress distribution output by CAE is output in the form of a color contour map. The output is therefore a stress. On the other hand, it is a luminescent brightness distribution that is obtained by measuring an object to be measured that has a mechanoluminescent substance applied thereon. Thus, the comparison can be difficult.

In view of the situation, the present invention provides a strain amount calculation system, a strain amount calculation method, and a storage medium that allow a mechanoluminescent brightness distribution based on an image to be output as a color contour map.

A strain amount calculation system according to a first aspect of the present invention includes an imaging unit that serially takes images of an object having a mechanoluminescent substance applied thereon, and a strain amount calculation device that is configured to acquire an image taken by the imaging unit, measure luminescent brightness from the acquired image, calculate an amount of strain on the object caused by a load on the object, based on a temporal change in the measured luminescent brightness, and output information on the calculated strain amount.

A strain amount calculation method according to a second aspect of the present invention is a method of calculating an amount of strain on an object based on luminescent brightness of a mechanoluminescent substance, and includes: serially taking images of the object; measuring luminescent brightness from an image taken by the image taking; calculating an amount of strain on the object caused by a load on the object, based on a temporal change in the luminescent brightness measured by the measuring; and outputting the strain amount calculated by the calculating.

A non-transitory readable storage medium that stores a program according to a third aspect of the present invention includes the program configured to allow a computer to realize the following: an imaging function of serially taking images of an object having a mechanoluminescent substance applied thereon; a measurement function of measuring luminescent brightness from an image taken by the imaging function; a calculation function of calculating an amount of strain on the object caused by a load on the object, based on a temporal change in the luminescent brightness measured by the measurement function; and an output function of outputting the strain amount calculated by the calculation function.

In the strain amount calculation system, the strain amount calculation device may be configured to divide the object into predetermined areas and calculate an amount of strain in each of the predetermined areas.

In the strain amount calculation system, the strain amount calculation device may be configured to calculate the strain amount by using, as reference luminescent brightness, luminescent brightness measured with no load put on the object.

In the strain amount calculation system, the strain amount calculation device may be configured to calculate the strain amount based on an assumption that luminescent brightness to be calculated is a value resulting from adding, to the reference luminescent brightness, a value obtained by superimposing a strain amount, a strain rate that is a temporal change in the strain amount, and a predetermined coefficient.

In the strain amount calculation system, the strain amount calculation device may be configured to output, as the information on the strain amount, an image of the object obtained by rendering the strain amount as a color contour map.

The strain amount calculation system according to the first aspect of the present invention can calculate a strain amount based on a temporal change in mechanoluminescent brightness, and therefore can output a mechanoluminescent brightness distribution as a stress distribution in the form of a color contour map.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

A strain amount calculation device according to an embodiment of the present invention will be described below in detail with reference to the drawings.

Embodiment

Configuration

Figure 1:
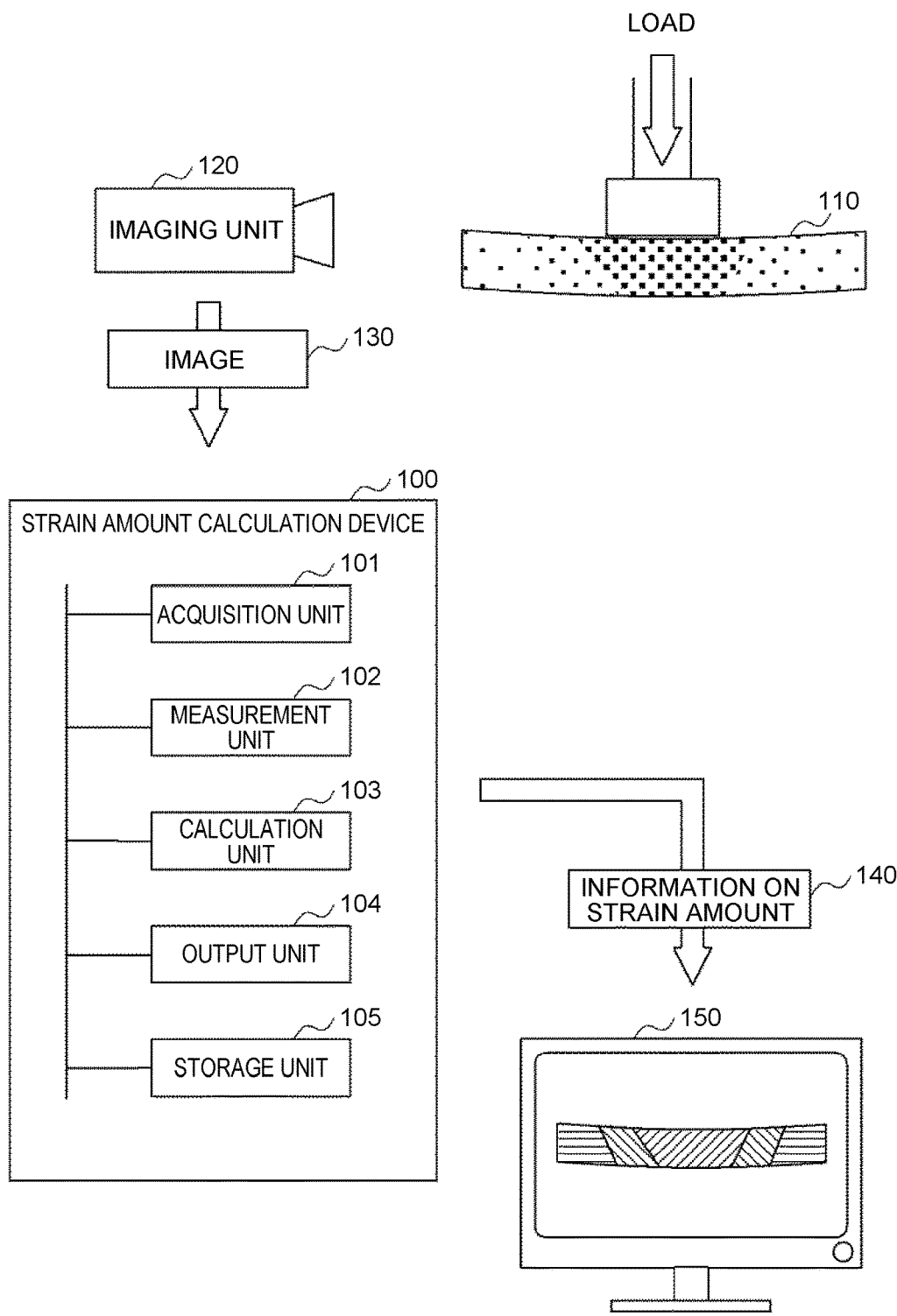
FIG. 1 is a view showing an example of the configuration of a strain amount calculation system.
Figure 2:
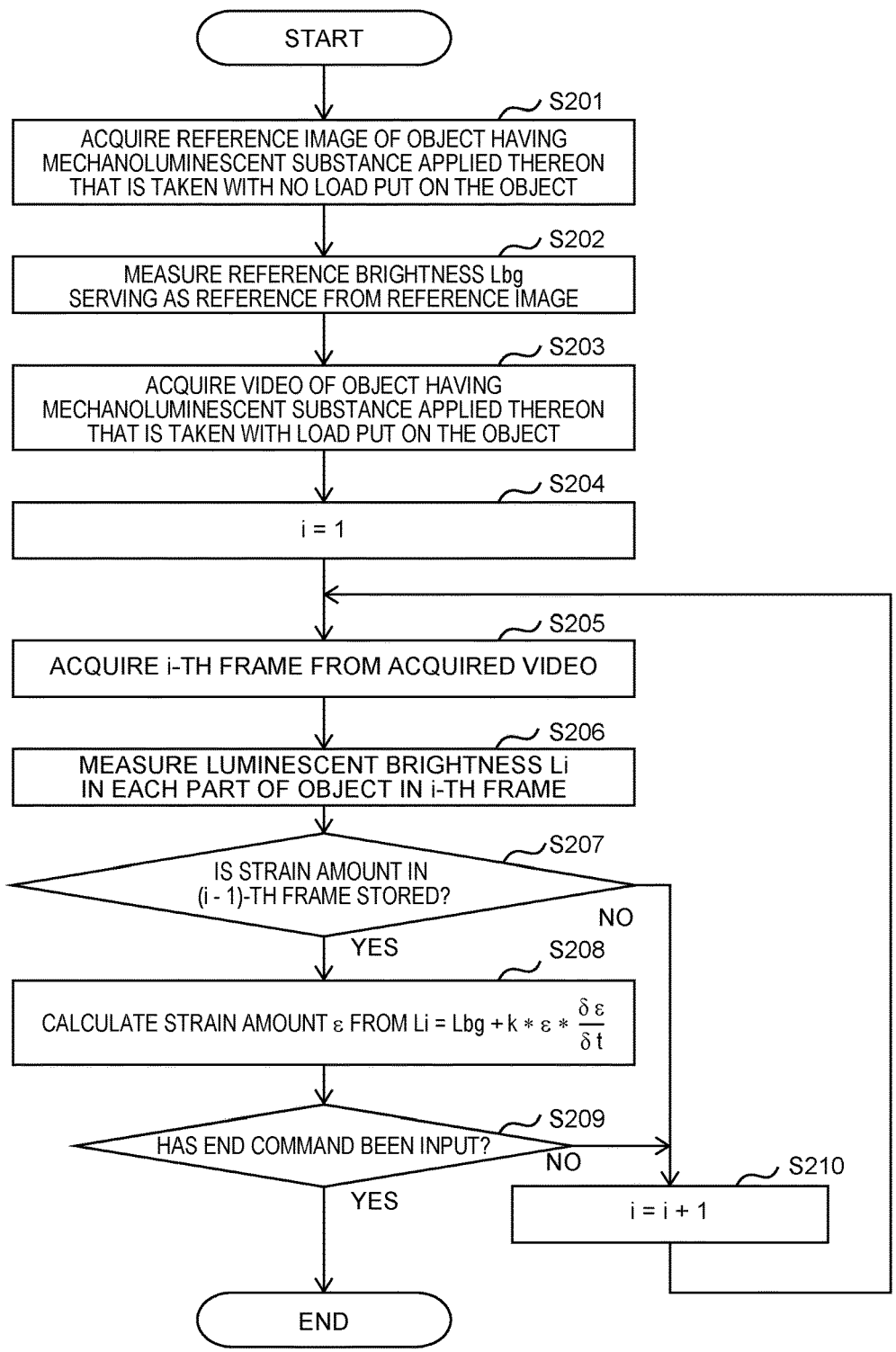
FIG. 2 is a flowchart showing the operation of a strain amount calculation device.

FIG. 1 is a view showing the configuration of a strain amount calculation system including a strain amount calculation device 100. In the strain amount calculation system, an imaging unit 120 takes images of an object 110 having a mechanoluminescent substance applied thereon, and the strain amount calculation device 100 calculates an amount of strain (stress) on the object 110 based on luminescent brightness from an image 130 obtained by imaging. Then, a display device 150 displays an image of the object 110 rendered as a color contour map based on the strain amount calculated by the strain amount calculation device 100. The strain amount calculation device 100 in the system will be described in detail below.

As shown in FIG. 1, the strain amount calculation device 100 includes an acquisition unit 101, a measurement unit 102, a calculation unit 103, an output unit 104, and a storage unit 105.

The acquisition unit 101 is a communication interface having a function of acquiring the image 130 taken by the imaging unit 120 that serially takes images of the object 110 having a mechanoluminescent substance applied thereon. The acquisition unit 101 may directly receive a video taken by the imaging unit 120, or may acquire a video that is taken by the imaging unit 120 and then stored in a server (not shown) etc. connected to the imaging unit 120 through a network. The acquisition unit 101 may be connected to the imaging unit 120 or an external server through a wired or wireless network, and as long as the image 130 can be acquired, any communication protocol may be used for communication. The acquisition of the image 130 by the acquisition unit 101 may be acquisition of images serially taken by the imaging unit 120, or may be acquisition of frames in series as images from a video taken by the imaging unit 120.

The object 110 for stress measurement may be any object that has a mechanoluminescent substance attached to a surface.

Here, a mechanoluminescent substance (a paint or a material) is a substance that emits light when loads, such as friction, impact, vibration, compression, tension, or torsion, are applied thereto as mechanical stimulus. Mechanoluminescence refers to a phenomenon of light emission with brightness according to a load (stress) applied.

For example, strontium aluminate (SrAl2O4: Eu) that is structurally controlled by doping with europium, or zinc sulfide (ZnS: Mn), barium calcium titanate ((Ba, Ca) TiO3: Pr), or calcium yttrium aluminate (CaYAl3O7: Ce), doped with a transition metal or a rare earth, can be used as the mechanoluminescent substance. However, the mechanoluminescent substance is not limited to these examples, and any substance that emits light with brightness according to a stress can be used.

The measurement unit 102 has a function of measuring (calculating) the brightness of the mechanoluminescent substance applied to the object 110 from the image 130 acquired by the acquisition unit 101. The measurement unit 102 retains in advance a coefficient of conversion between brightness obtained from the image 130 taken by the imaging unit 120 and the actual brightness, and can calculate the value of the actual brightness by multiplying a value of brightness of each pixel of the image 130 by the conversion coefficient. For example, the measurement unit 102 can be realized by a processor that reads out and executes a brightness value calculation program stored in advance in the storage unit 105 of the strain amount calculation device 100.

The calculation unit 103 has a function of calculating an amount of strain (stress) on the object 110 caused by a load on the object 110, based on a temporal change in the luminescent brightness measured by the measurement unit 102. The intensity (brightness) of mechanoluminescence can be expressed as background light+(strain amount×strain rate). More specifically, brightness L (t) that is brightness at time t can be expressed by the following Expression (1):

$$L(t) = L_{bg} + k\varepsilon \frac{\partial \varepsilon}{\partial t} \quad (1)$$

In Expression (1), L (t) denotes a value of brightness measured by the measurement unit 102. The symbol Lbg denotes reference luminescent brightness serving as a reference, which is a value of brightness of the object 110 when no light emission is induced by a stress and which corresponds to the aforementioned background light. The symbol k denotes a predetermined coefficient. Methods of determining the coefficient k include, but are not limited to, the following: exciting, to a certain level, a substance which has a specific reflectance and to which a mechanoluminescent paint has been applied in advance to a certain thickness, and then simultaneously measuring brightness that can be acquired by an imaging device and a strain amount at that time with a strain gauge etc. (calibration at arbitrary points). In Expression (1), $\varepsilon$ denotes a strain amount, and $\delta\varepsilon/\delta t$ denotes a strain rate. The strain rate means a temporal change in strain. The calculation unit 103 calculates the strain amount $\varepsilon$ using Expression (1). The calculation unit 103 uses Expression (1) for each predetermined area of the image to calculate an amount of strain in the predetermined area. The predetermined area here is an area of one pixel as an example, but the predetermined area is not limited to the example. The predetermined area may include a plurality of pixels, and in this case, an average value of values of brightness of the pixels may be used as the value of brightness in the predetermined area.

To calculate the strain amount $\varepsilon$ (i) in an i-th (time t) frame by Expression (1), Expression (1) can be modified into the following Expression (2) by using a strain amount $\varepsilon$ (i−1) calculated for an (i−1)-th (time (t−1)) frame:

$$L(i) = L_{bg} + k\varepsilon(i)\frac{(\varepsilon(i) - \varepsilon(i-1))}{t - (t-1)} \quad (2)$$

The following Expression (3) can be derived by modifying Expression (2):

$$\frac{L(i) - L_{bg}}{k} = \varepsilon(i)^2 - \varepsilon(i) \times \varepsilon(i-1) \quad (3)$$

In Expression (3), L (i) is a known value measured by the measurement unit 102, and Lbg is a known value that is reference luminescent brightness measured in advance. Being a predetermined coefficient, k is also a known value. Moreover, ε (i−1) is also a known value, as it is the strain amount calculated for the (i−1)-th frame. Thus, ε (i) is the only one unknown value in Expression (3). The calculation unit 103 can calculate the strain amount ε (i) for the i-th frame by solving the quadratic equation of Expression (3).

For example, the calculation unit 103 can be realized by a processor that reads out and executes a strain amount calculation program stored in advance in the storage unit 105 of the strain amount calculation device 100. Further specific examples of the calculation of a strain amount will be described later.

The output unit 104 is a communication interface having a function of outputting information on a strain amount calculated by the calculation unit 103. The output unit 104 may be connected to the external display device 150 through a wired or wireless network, and as long as the output unit 104 can transmit information on a strain amount, any communication protocol may be used for communication. Here, the information on a strain amount may be the value of a strain amount calculated by the calculation unit 103 as is, or may be information on a value of a strain amount having been processed (e.g., an image of a value of a strain amount rendered as a color contour map). To output information on a strain amount having been processed, the strain amount calculation device 100 may include an image generation unit (not shown) that generates an image of the object 110 rendered as a color contour map based on a strain amount in pixel units calculated by the calculation unit 103. As in the conventional CAE, the image generation unit can generate an image of the object 110 rendered as a color contour map based on a stress (strain amount).

Based on the information on a strain amount output by the output unit 104, the display device 150 can display the object 110, for example, as a color contour image showing a stress distribution. The display device 150 can be realized by a commonly known display such as an LCD or an organic EL display. Other than such displays, a monitor of a mobile terminal, a monitor of a tablet terminal, etc. can also be used as the display device 150, for example.

The storage unit 105 is a storage medium that has a function of storing various data and programs required for the operation of the strain amount calculation device 100. The storage unit 105 can be realized by, for example, a hard disc drive (HDD), a solid state drive (SSD), a flash memory, etc., but is not limited to these examples. For example, the storage unit 105 stores a measurement program that allows the measurement unit 102 to calculate the luminescent brightness of each pixel from the image 130, a strain amount calculation program that allows the calculation unit 103 to calculate a strain amount, and a strain amount calculated by the calculation unit 103.

This concludes the description of the configuration of the strain amount calculation device 100.

Operation

Now, the operation of the strain amount calculation device 100 related to the calculation of a strain amount will be described.

Step S201

In step S201, the acquisition unit 101 of the strain amount calculation device 100 acquires a reference image (which may be a 0th (first) frame of a video) of the object 110 on which a strain amount is to be calculated and which has a mechanoluminescent substance applied thereon. The reference image is taken with no load put on the object 110. The acquisition unit 101 transfers the acquired reference image to the measurement unit 102, and then the strain amount calculation device 100 proceeds to step S202.

Step S202

In step S202, the measurement unit 102 measures the reference brightness Lbg, which serves as a reference, in each of the pixels (predetermined areas) composing the reference image transferred from the acquisition unit 101, and then the strain amount calculation device 100 proceeds to step S203.

Step S203

In step S203, the acquisition unit 101 acquires, from the imaging unit 120, a video of a state (process) in which a load is put on the object 110 having a mechanoluminescent paint applied thereon, and then the strain amount calculation device 100 proceeds to step S204.

Step S204

In step S204, the strain amount calculation device 100 returns the frame number i related to the process to the default value 1, and then proceeds to step S205.

Step S205

In step S205, the measurement unit 102 acquires the i-th frame from the video transferred thereto, and then the strain amount calculation device 100 proceeds to step S206.

Step S206

In step S206, the measurement unit 102 measures the luminescent brightness Li in each predetermined area (each pixel) of the object 110 in the i-th frame, and then the strain amount calculation device 100 proceeds to step S207.

Step S207

In step S207, the calculation unit 103 determines whether the strain amount ε (i−1) calculated for the (i−1)-th frame is stored in the storage unit 105. When the strain amount ε (i−1) is stored (YES), the strain amount calculation device 100 proceeds to step S208, and when the strain amount ε (i−1) is not stored (NO), the strain amount calculation device 100 proceeds to step S210.

Step S208

In step S208, the calculation unit 103 calculates the strain amount ε (i) in each pixel of the i-th frame measured by the measurement unit 102 by using Expressions (1) and (3). Then, the strain amount calculation device 100 proceeds to step S209.

Step S209

In step S209, the strain amount calculation device 100 determines whether a command for ending the strain amount calculation process has been input. When the command has been input (YES), the strain amount calculation device 100 ends the process. When the command has not been input (NO), the strain amount calculation device 100 proceeds to step S210.

Step S210

In step S210, the strain amount calculation device 100 adds 1 to the frame number i, and then returns to step S205.

Specific Example of Calculation of Strain Amount

Now, the calculation of a strain amount will be specifically described using a specific example.

Figure 3A:
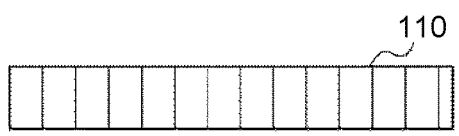
FIG. 3A is a view showing an example of a mechanoluminescent state when no load is put on an object.
Figure 3B:
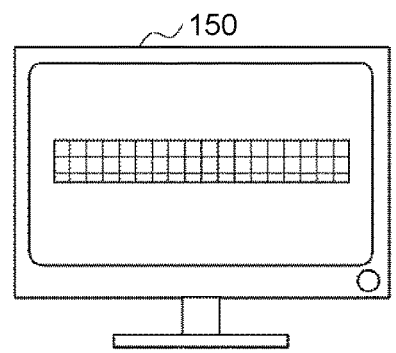
FIG. 3B is a view showing an example of a stress distribution in the object shown in FIG. 3A output in the form of a color contour map.

First, the luminescent brightness of the object 110 is measured with no load put on the object 110 (the state shown in FIG. 3A). The luminescent brightness in this state is regarded as "zero". Accordingly, the reference luminescent brightness Lbg can be disregarded as zero. In practice, the measured value is used as the reference luminescent brightness Lbg, and a value obtained by subtracting the reference luminescent brightness Lbg from a subsequent value of luminescent brightness measured with a load put on the object is used. For example, a color contour map output in this case is a color contour map showing a uniform stress distribution as shown in FIG. 3B.

Figure 3C:
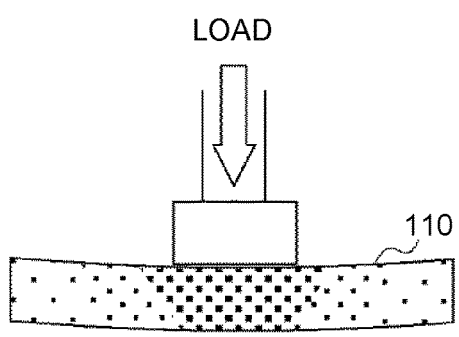
FIG. 3C is a view showing an example of a mechanoluminescent state when a load is put on the object.

Next, as shown in FIG. 3C, when a load is put on the object 110, the mechanoluminescent substance emits light according to the stress. Here, the mechanoluminescent brightness 1/60 of a second after the load starts to be applied is assumed to be "1". At the point in time of 1/60 of a second, the preceding strain amount ε (i−1) is the strain amount at time "zero" and is therefore "zero". Assigning the values to Expression (2) results in the following Relation Expression (4):

$$L\left(\frac{1}{60}\right) = k\varepsilon\left(\frac{1}{60}\right)\frac{\varepsilon\left(\frac{1}{60}\right)}{\frac{1}{60}} \quad (4)$$

To simplify the description, the coefficient k is assumed to be 1/60. Then, from L (1/60)=1, a relational expression ε (1/60)²=1 can be obtained. The positive solution of the relational expression can be obtained as the strain amount ε (1/60) at the point in time of 1/60 of a second. Thus, in this example, ε (1/60)=1 can be obtained.

Next, the value of luminescent brightness measured by the measurement unit 102 after 2/60 of a second is assumed to be "20". Then, the following Relation Expression (5) can be obtained:

$$L\left(\frac{2}{60}\right) = k\varepsilon\left(\frac{2}{60}\right)\frac{\varepsilon\left(\frac{2}{60}\right) - \varepsilon\left(\frac{1}{60}\right)}{\frac{2}{60} - \frac{1}{60}} \quad (5)$$

$$= \frac{1}{60}\varepsilon\left(\frac{2}{60}\right)\frac{\varepsilon\left(\frac{2}{60}\right) - 1}{\frac{1}{60}}$$

$$= \varepsilon\left(\frac{2}{60}\right)^2 - \varepsilon\left(\frac{2}{60}\right)$$

Since the value of luminescent brightness at the point in time of L (2/60) is 20, ε (2/60)=−4 or 5 is obtained. Using the positive value of the values as the solution, the calculation unit 103 can obtain "5" as the strain amount ε (2/60) at the point in time of 2/60 of a second.

Next, the luminescent brightness measured by the measurement unit 102 after 3/60 of a second is assumed to be 50. In this case, the strain amount ε (3/60) can be obtained in a similar manner by solving the following Expression (6):

$$L\left(\frac{3}{60}\right) = k\varepsilon\left(\frac{3}{60}\right)\frac{\varepsilon\left(\frac{3}{60}\right) - \varepsilon\left(\frac{2}{60}\right)}{\frac{3}{60} - \frac{2}{60}} \quad (6)$$

$$= \varepsilon\left(\frac{3}{60}\right)^2 - 5\varepsilon\left(\frac{3}{60}\right) = 50$$

The calculation unit 103 obtains ε (3/60)=10 by solving Expression (6). Therefore, when the coefficient k is a time difference, the reference luminescent brightness Lbg is zero, and the luminescent brightness measured by the measurement unit 102 is a, the calculation unit 103 can solve the quadratic expression of the following Expression (7) to obtain the positive solution as the strain amount ε (i):

$$\varepsilon(i)^2 - \varepsilon(i) \times \varepsilon(i-1) = a \quad (7)$$

Figure 3D:
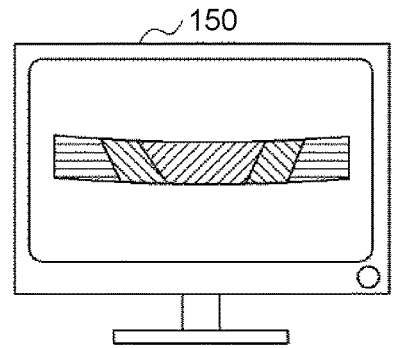
FIG. 3D is a view showing an example of a stress distribution in the object shown in FIG. 3C output in the form of a color contour map.

As a result, for example, an image of the object 110 rendered as a color contour map based on the calculated strain amount can be output as shown in FIG. 3D.

CONCLUSION

The strain amount calculation device 100 can calculate an amount of strain on an object from a temporal change in mechanoluminescent brightness. Therefore, the strain amount calculation device 100 can generate an image of a stress distribution in the object rendered as a color contour map based on the calculated strain amount. Thus, it becomes possible to verify a stress distribution obtained by CAE through a comparison between a color contour image of a stress distribution obtained by CAE and a color contour image based on a strain amount calculated by the strain amount calculation device 100. Moreover, by checking a color contour image based on a strain amount calculated by the strain amount calculation device 100, a user can recognize any load that is applied to some area but the user has failed to notice in a stress distribution obtained by CAE.

SUPPLEMENTARY NOTE

It should be understood that the strain amount calculation device according to the above embodiment is not limited to this embodiment but may also be realized by other techniques. In the following, various modified examples will be described.

In the above embodiment, the imaging unit 120 is a device outside the strain amount calculation device 100, but the strain amount calculation device 100 may also include the imaging unit 120.

In the above embodiment, the display device 150 is a device outside the strain amount calculation device 100, but the strain amount calculation device 100 may also include the display device 150.

In the above embodiment, in the case where the strain amount calculation device 100 outputs a strain amount as is, the display device 150 or a computation device connected to the display device 150 that receives the strain amount may have a function of generating an image of the object 110 rendered as a color contour map based on the received strain amount.

In the above embodiment, the case where the strain amount is calculated every 1/60 of a second has been shown as a specific example, but the calculation interval is of course not limited to this example. For example, the calculation interval may be every 1/20 of a second or every 1/90 of a second.

In the above embodiment, the measurement unit 102 measures the value of brightness of each pixel from the image 130. However, instead of this technique, a brightness sensor may be used for the measurement.

Figure 4:
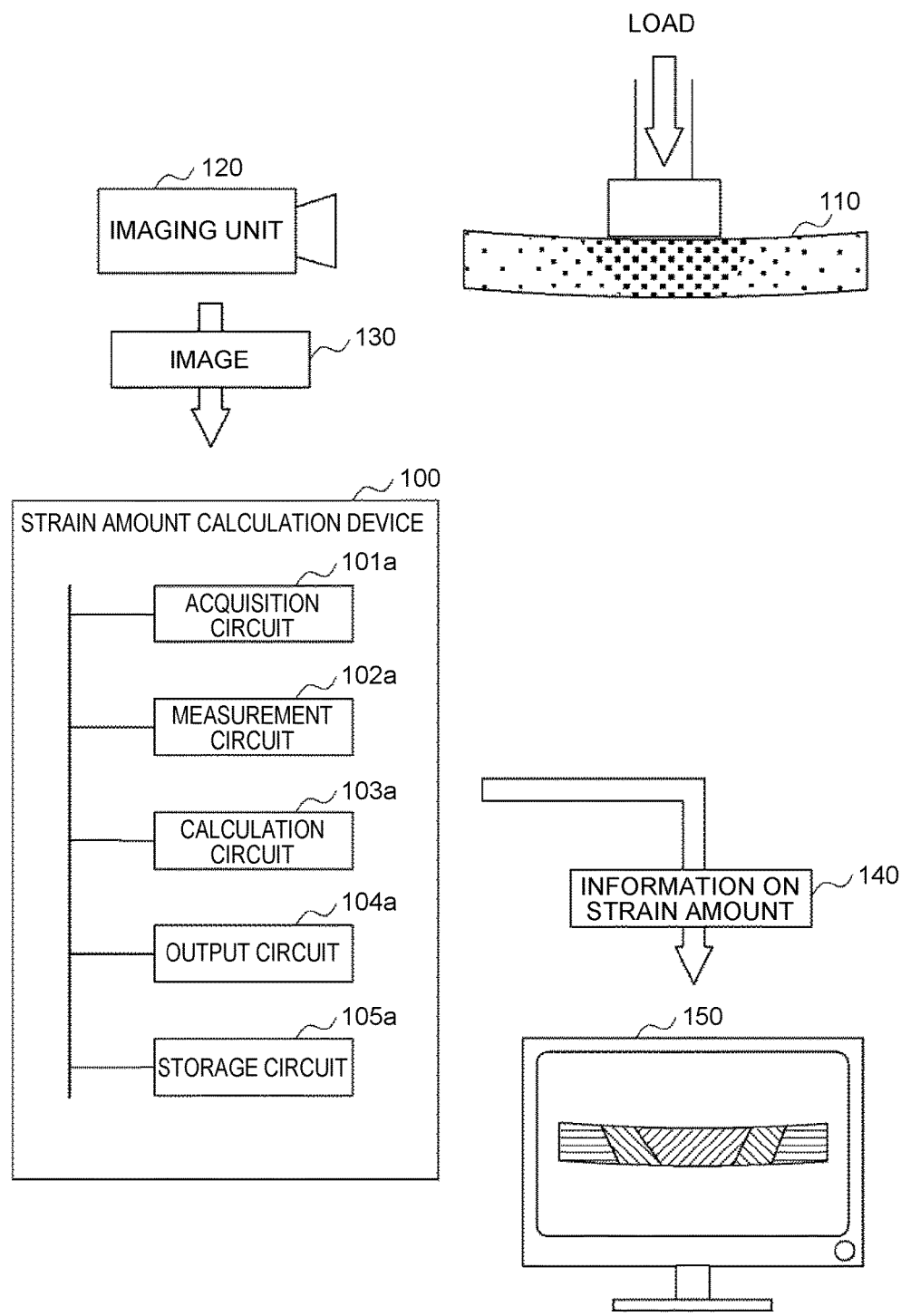
FIG. 4 is a block diagram showing an example of the functional configuration of the strain amount calculation device.

In the above embodiment, the technique employed by the strain amount calculation device to calculate a strain amount involves the processors that function as the functional units composing the strain amount calculation device 100 and execute the strain amount calculation program etc. to calculate a strain amount. The processors may be realized in the strain amount calculation device by a logic circuit (hardware) or a dedicated circuit formed in an integrated circuit (IC) chip, a large-scale integration (LSI), etc. Moreover, such a circuit may be realized by a single or a plurality of integrated circuits, and the functions of the plurality of functional units shown in the above embodiment may be realized by a single integrated circuit. LSIs are also referred to as VLSIs, super LSIs, ultra LSIs, etc. according to the difference in the degree of integration. Specifically, as shown in FIG. 4, the functional units composing the strain amount calculation device 100 may be realized by a physical circuit. As shown in FIG. 4, the strain amount calculation device 100 includes an acquisition circuit 101a, a measurement circuit 102a, a calculation circuit 103a, an output circuit 104a, and a storage circuit 105a, and each circuit has the same function as the functional unit of the same name in the above embodiment.

The strain amount calculation program may be recorded in a storage medium that can be read by a processor. A "non-transitory tangible medium," for example, a tape, disc, card, semiconductor memory, or programmable logic circuit, can be used as the storage medium. The strain amount calculation program may be supplied to the processor through an arbitrary transfer medium (a communication network, a broadcast wave, etc.) that can transfer the strain amount calculation program. The strain amount calculation program of the present invention can also be realized in the form of a data signal embedded in a carrier wave that is embodied by electronic transmission.

The strain amount calculation program can be implemented using, for example, a script language such as Action-Script or JavaScript (R), an object-oriented programming language such as Objective-C or Java (R), or a markup language such as HTML5.

The constituent elements shown in the above embodiment and supplementary note may be combined as appropriate.

What is claimed is:

1. A strain amount calculation system comprising:
   an imaging unit configured to capture a plurality of sequential images of an object having a mechanoluminescent substance applied to the object; and
   a strain amount calculation processor configured to:
      acquire an image of the plurality of sequential images captured by the imaging unit,
      measure luminescent brightness from the acquired image,
      calculate an amount of strain on the object caused by a load on the object, based on a temporal change in the measured luminescent brightness, and
      output an image of the object illustrating the calculated amount of strain on the object as a rendered color contour map on the object.

2. The strain amount calculation system according to claim 1, wherein the strain amount calculation processor is configured to divide the object into predetermined areas and calculate an amount of strain in each of the predetermined areas.

3. The strain amount calculation system according to claim 2, wherein the strain amount calculation processor is configured to calculate the strain amount by using, as reference luminescent brightness, luminescent brightness measured with no load put on the object.

4. The strain amount calculation system according to claim 1, wherein the strain amount calculation processor is configured to calculate the strain amount by using, as reference luminescent brightness, luminescent brightness measured with no load put on the object.

5. The strain amount calculation system according to claim 4, wherein the strain amount calculation processor is configured to calculate the strain amount based on an assumption that luminescent brightness to be calculated is a value resulting from adding, to the reference luminescent brightness, a value obtained by superimposing a strain amount, a strain rate that is a temporal change in the strain amount, and a predetermined coefficient.

6. The strain amount calculation system according to claim 3, wherein the strain amount calculation processor is configured to calculate the strain amount based on an assumption that luminescent brightness to be calculated is a value resulting from adding, to the reference luminescent brightness: (i) a value obtained by superimposing a strain amount, (ii) a strain rate that is a temporal change in the strain amount, and (iii) a predetermined coefficient.

7. A strain amount calculation method to calculate an amount of strain on an object based on luminescent brightness of a mechanoluminescent substance, the method comprising:
   capturing a plurality of sequential images of the object;
   measuring luminescent brightness from an image of the plurality of sequential images;
   calculating an amount of strain on the object caused by a load on the object, based on a temporal change in the luminescent brightness measured by the measuring; and
   outputting an image of the object illustrating the calculated amount of strain on the object as a rendered color contour map on the object.

8. A non-transitory readable storage medium having stored therein a program, the program causing a computer to:
   capture a plurality of sequential images of an object having a mechanoluminescent substance applied thereon;
   measure luminescent brightness from an image of the plurality of sequential images;
   calculate an amount of strain on the object caused by a load on the object, based on a temporal change in the luminescent brightness measured by the measurement function; and
   output an image of the object illustrating the calculated amount of strain on the object as a rendered color contour map on the object.

* * * * *